(12) United States Patent
Chono

(10) Patent No.: US 8,262,572 B2
(45) Date of Patent: Sep. 11, 2012

(54) ULTRASONIC DIAGNOSTIC APPARATUS AND IMAGE PROCESSING APPARATUS FOR ULTRASONIC DIAGNOSIS

(75) Inventor: Tomoaki Chono, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/121,263

(22) PCT Filed: Oct. 2, 2009

(86) PCT No.: PCT/JP2009/067211
§ 371 (c)(1),
(2), (4) Date: Mar. 28, 2011

(87) PCT Pub. No.: WO2010/038848
PCT Pub. Date: Apr. 8, 2010

(65) Prior Publication Data
US 2011/0178405 A1    Jul. 21, 2011

(30) Foreign Application Priority Data
Oct. 3, 2008    (JP) ................................. 2008-258822

(51) Int. Cl.
*A61B 8/00*    (2006.01)
(52) U.S. Cl. .................... 600/437; 382/128; 382/131
(58) Field of Classification Search .......... 600/437–469; 328/130–132
See application file for complete search history.

(56) References Cited

U.S. PATENT DOCUMENTS

| | | | |
|---|---|---|---|
| 6,755,791 B2* | 6/2004 | Kawashima | 600/467 |
| 7,110,583 B2* | 9/2006 | Yamauchi | 382/128 |
| 7,474,778 B2* | 1/2009 | Shinomura et al. | 382/131 |
| 7,693,251 B2* | 4/2010 | Kono et al. | 376/252 |
| 7,828,731 B2* | 11/2010 | Baba et al. | 600/437 |
| 2002/0102023 A1* | 8/2002 | Yamauchi | 382/199 |
| 2003/0199756 A1* | 10/2003 | Kawashima | 600/424 |
| 2004/0144176 A1* | 7/2004 | Yoden | 73/628 |
| 2004/0210137 A1* | 10/2004 | Baba et al. | 600/443 |
| 2005/0124880 A1* | 6/2005 | Shinomura et al. | 600/437 |
| 2007/0038103 A1* | 2/2007 | Kobayashi | 600/443 |
| 2008/0177183 A1* | 7/2008 | Courtney et al. | 600/463 |
| 2009/0137904 A1* | 5/2009 | Wu et al. | 600/447 |
| 2009/0247879 A1* | 10/2009 | Angelsen et al. | 600/463 |
| 2010/0160783 A1* | 6/2010 | Halmann et al. | 600/447 |
| 2011/0102429 A1* | 5/2011 | Matsumoto et al. | 345/419 |
| 2011/0245670 A1* | 10/2011 | Tashiro et al. | 600/443 |
| 2011/0295118 A1* | 12/2011 | Okamura | 600/440 |

FOREIGN PATENT DOCUMENTS

JP    08-131403    5/1996
(Continued)

*Primary Examiner* — Sanjay Cattungal
(74) *Attorney, Agent, or Firm* — Antonelli, Terry, Stout & Kraus, LLP.

(57) ABSTRACT

An ultrasonic diagnostic apparatus including means that acquires a three-dimensional ultrasonic signal of an internal organ of an examinee, means that sets a direction of a two-dimensional standard cross-section of the internal organ; means that adjusts display parameter of an image of a site which an examinee intends to observe, means that generates a two-dimensional standard cross-sectional image from the three-dimensional ultrasonic signal on the basis of the set direction of the two-dimensional standard cross-section of the internal organ, means that generates an observation cross-sectional image and a rendering image from the three-dimensional ultrasonic signal on the basis of the display parameters of the adjusted image, and display means that combines and displays the two-dimensional standard cross-sectional image, the observation cross-sectional image and the rendering image.

15 Claims, 12 Drawing Sheets

FOREIGN PATENT DOCUMENTS

| | | |
|---|---|---|
| JP | 2001-128975 | 5/2001 |
| JP | 2004-141522 | 5/2004 |
| JP | 2006-526451 | 11/2006 |
| JP | 2008-534082 | 8/2008 |

\* cited by examiner (a) CARDIAC APEX LONG AXIS IMAGE (b) CARDIAC APEX 2-CAVITY IMAGE (c) CARDIAC APEX 4-CAVITY IMAGE (d) PARASTERNAL LONG AXIS IMAGE (e) PARASTERNAL SHORT AXIS IMAGE

ULTRASONIC DIAGNOSTIC APPARATUS AND IMAGE PROCESSING APPARATUS FOR ULTRASONIC DIAGNOSIS

TECHNICAL FIELD

The present invention relates to an ultrasonic diagnostic apparatus and an image processing apparatus for ultrasonic diagnosis in which the position of a cross-section of a site which an examiner intends to observe is set from an ultrasonic three-dimensional signal in ultrasonic three-dimensional image diagnosis for an examinee's internal organ including a heart, and an image of the site is displayed.

BACKGROUND ART

Display and measurement are three-dimensionally displayed in ultrasonic three-dimensional image diagnosis of a heart, and thus an examination efficiency has been required to be enhanced by displaying and operating methods which are not troublesome for an examiner and also are easily understandable by the examiner. Information which the examiner intends to observe is a part of three-dimensional data containing a large amount of information, and a technique of handling this information efficiently is required. At present, there has been required an operation of subjecting a three-dimensional image to rendering display, rotating or enlarging/reducing the three-dimensional image by using input equipment such as a trackball and adjusting a rendering threshold value, thereby acquiring a desired image while searching.

As a technique of enhancing the efficiency of measurement setting in three-dimensional measurement, a system has been proposed in which a two-dimensional image extracted from three-dimensional data by an apparatus is displayed to set a measurement target area, and an examiner manually operates input equipment such as a joystick to adjust the position of a measurement target region while observing the two-dimensional image in Patent Document 1.

PRIOR ART DOCUMENT

Patent Document

Patent Document 1: JP-A-2001-128975

SUMMARY OF THE INVENTION

Problem to be Solved by the Invention

In order to display a three-dimensional image, it is required to determine the position and direction of a cross-section which an examiner wishes to observe, parameters for rendering, etc. According to the method of the above Patent Document 1, an operation is required in which an apparatus extracts a two-dimensional image from three-dimensional data and displays the two-dimensional image and an examiner adjusts the position of a measurement target area while observing the two-dimensional image. Therefore, it is required to further enhance the operation efficiency.

Therefore, according to the present invention, there is provided an ultrasonic diagnostic apparatus and an image processing apparatus for ultrasonic diagnosis in which the positional relationship between a probe and an internal organ is determined, and various kinds of display parameters of a cross-section which an examiner wishes to observe are determined to perform display processing of a three-dimensional ultrasonic image of the internal organ.

Means of Solving the Problem

An ultrasonic diagnostic apparatus according to the present invention of claim 1 which is implemented to solve the above problem is characterized by comprising: means that acquires a three-dimensional ultrasonic signal of an internal organ of an examinee; means that sets a direction of a two-dimensional standard cross-section of the internal organ; means that adjusts display parameter of an image of a site which an examinee intends to observe; means that generates a two-dimensional standard cross-sectional image from the three-dimensional ultrasonic signal on the basis of the set direction of the two-dimensional standard cross-section of the internal organ; means that generates an observation cross-sectional image and a rendering image from the three-dimensional ultrasonic signal on the basis of the display parameters of the adjusted image; and display means that combines and displays the two-dimensional standard cross-sectional image, the observation cross-sectional image and the rendering image.

According to the present invention having the feature as described above, the positional relationship between a probe and the internal organ is recognized by setting the direction of the two-dimensional standard cross-section of the internal organ in the thus-acquired three-dimensional ultrasonic signal of the internal organ of the examinee. The display parameters of the image corresponding to the site which the examiner intends to observe are adjusted, and thus the apparatus can display the three-dimensional image.

Furthermore, an image processing apparatus for ultrasonic diagnosis according to the present invention is an image processing apparatus used to process a three-dimensional ultrasonic signal of an internal organ of an examinee that is characterized by comprising: means that sets a direction of a two-dimensional standard cross-section of the internal organ; means that adjusts display parameter of an image of a site which an examinee intends to observe; means that generates a two-dimensional standard cross-sectional image from the three-dimensional ultrasonic signal of the internal organ on the basis of the set direction of the two-dimensional standard cross-section of the internal organ; means that generates an observation cross-sectional image and a rendering image from the three-dimensional ultrasonic signal of the internal organ on the basis of the display parameters of the adjusted image; and display means that combines and displays the two-dimensional standard cross-sectional image, the observation cross-sectional image and the rendering image.

According to the present invention having the feature as described above, the positional relationship between a probe and the internal organ is recognized by setting the direction of the two-dimensional standard cross-section of the internal organ in the thus-acquired three-dimensional ultrasonic signal of the internal organ of the examinee. The display parameters of the image corresponding to the site which the examiner intends to observe are adjusted, and thus the apparatus can display the three-dimensional image.

Effect of the Invention

According to the present invention, as compared with conventional manual complicated image display adjustment which uses input equipment, the image display adjustment is performed with assistance of automatic or semi-automatic processing, whereby easiness of the operation can be enhanced and thus the load on the examiner in the ultrasonic examination operation can be reduced.

BEST MODES FOR CARRYING OUT THE INVENTION

Figure 11:
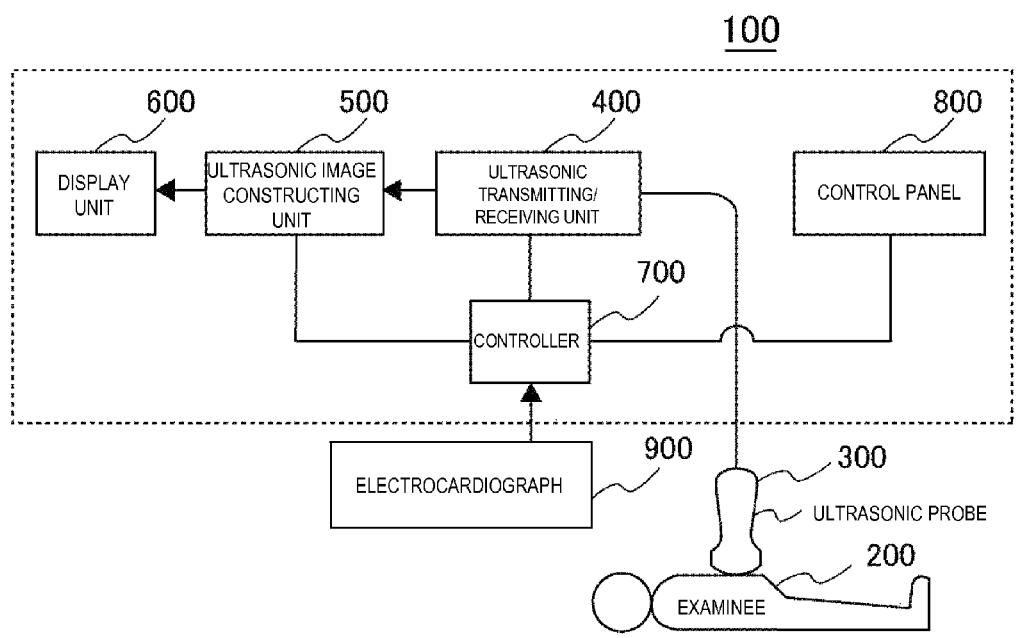
FIG. 11 is a block diagram showing an ultrasonic diagnostic apparatus to which the present invention is applied.

FIG. 11 is a block diagram showing an ultrasonic diagnostic apparatus to which the present invention is applied. An ultrasonic diagnostic apparatus 100 forms and displays an ultrasonic image by using a reflection echo signal acquired by transmitting/receiving an ultrasonic wave into an examinee 200, and it has an ultrasonic probe 300 having transducer elements for irradiating the examinee 200 with ultrasonic waves and receiving ultrasonic waves, an ultrasonic wave transmitting/receiving unit 400 for transmitting/receiving an ultrasonic signal, an ultrasonic image constructing unit 500 for constructing an ultrasonic image on the basis of a reception signal, a display unit 600 for displaying the constructed ultrasonic image, a controller 700 for controlling the respective constructions, a control panel 800 for supplying an instruction to the controller and an electrocardiograph 900 provided as occasion demands.

Figure 1:
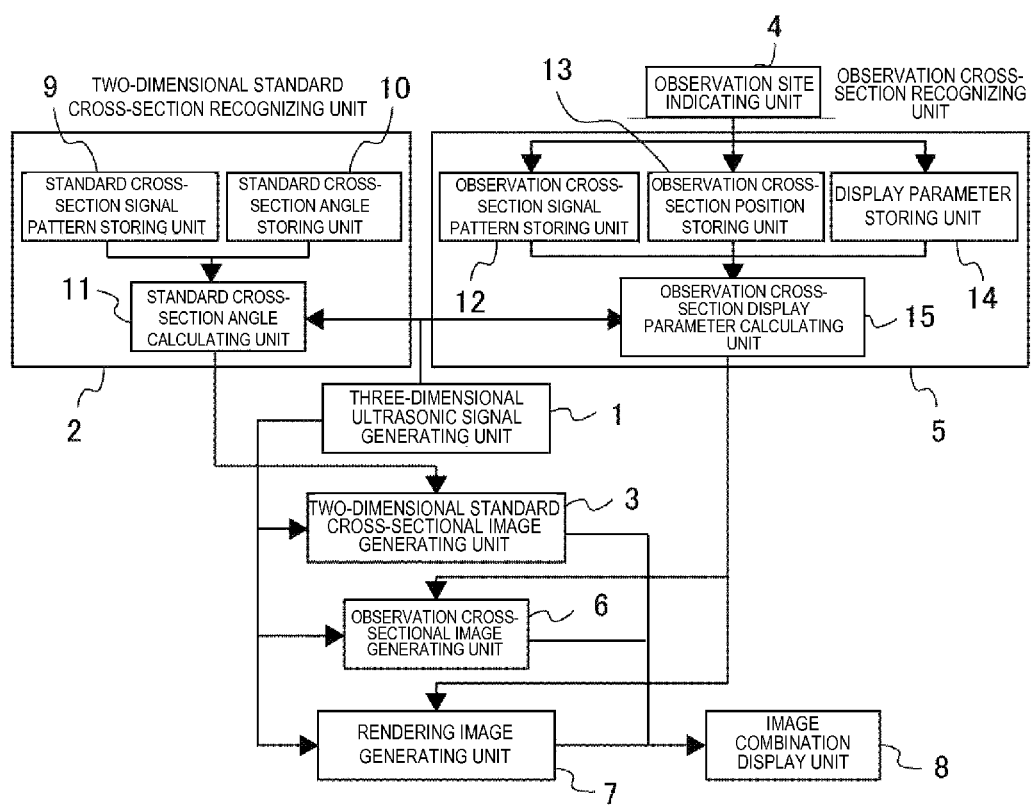
FIG. 1 is a block diagram showing the schematic construction of the present invention.

The present invention is particularly characterized in "ultrasonic image constructing unit 500" in the ultrasonic diagnostic apparatus of FIG. 11. The embodiment of this invention will be described with reference to FIG. 1. FIG. 1 is a block diagram showing an outline of the ultrasonic diagnostic apparatus according to the embodiment.

The ultrasonic diagnostic apparatus shown in FIG. 1 has a three-dimensional ultrasonic signal generating unit 1 constructed by a known ultrasonic probe, an ultrasonic wave transmitting/receiving unit, etc. a two-dimensional standard cross-section recognizing unit 2 for recognizing a two-dimensional standard cross-section from a three-dimensional signal, a two-dimensional standard cross-sectional image generating unit 3 for generating a two-dimensional standard cross-sectional image from the three-dimensional signal, an observation site indicating unit 4 for indicating an observation site by an examiner, an observation cross-section recognizing unit 5 for recognizing a cross-section containing the indicated site from a three-dimensional signal, an observation cross-sectional image generating unit 6 for generating an observation cross-sectional image from a three-dimensional signal, a rendering image generating unit 7 for generating a rendering image from a three-dimensional signal, and an image combination displaying unit 8 for combining and displaying the two-dimensional standard cross-sectional image, the observation cross-sectional image and the rendering image.

Furthermore, the two-dimensional standard cross-section recognizing unit 2 has a standard cross-section signal pattern storing unit 9 for storing a typical pattern of a two-dimensional standard cross-section signal, a standard cross-section angle storing unit 10 for storing an angle of a standard two-dimensional standard cross-section given as a rotational angle when the opening direction of a two-dimensional array probe is set as an axis, and a standard cross-section angle calculating unit 11 for recognizing a standard cross-section angle from the data of the storing unit. The observation cross-section recognizing unit 5 has an observation cross-section signal pattern storing unit 12 for storing a typical pattern of a two-dimensional observation cross-section signal, an observation cross-section position storing unit 13 for storing a standard position of the cross-section, a display parameter storing unit 14 for storing standard parameters for displaying the cross-section, and an observation cross-section display parameter calculating unit 15 for recognizing the position of the observation cross-section and the display parameters from the data of the storing unit.

The respective constituent elements will be described below.

The three-dimensional ultrasonic signal generating unit comprises a known ultrasonic probe, an ultrasonic wave transmitting/receiving unit, etc., and it receives backscattered waves from a living tissue by a connected two-dimensional array ultrasonic probe to generate three-dimensional ultrasonic signal data.

The two-dimensional standard cross-section recognizing unit 2 calculates the rotational angles of two-dimensional standard cross-sections 20, 21 and 22 contained in a cross-section group 19 rotating about the opening direction of the two-dimensional array probe (indicated by a broken line of FIG. 2) from the three-dimensional ultrasonic signal of the three-dimensional ultrasonic signal generating unit 1. In the two-dimensional standard cross-sectional image generating unit 3, the rotational angle is used to indicate the position (angle) of a two-dimensional standard cross-sectional image from the data of the three-dimensional ultrasonic signal to generate the two-dimensional standard cross-sectional image.

The two-dimensional standard cross-sectional image generating unit 3 generates an image of the two-dimensional cross-section whose rotational angle is calculated by the two-dimensional standard cross-section recognizing unit 2 from the three-dimensional ultrasonic signal acquired in the three-dimensional ultrasonic signal generating unit 1.

Figure 2:
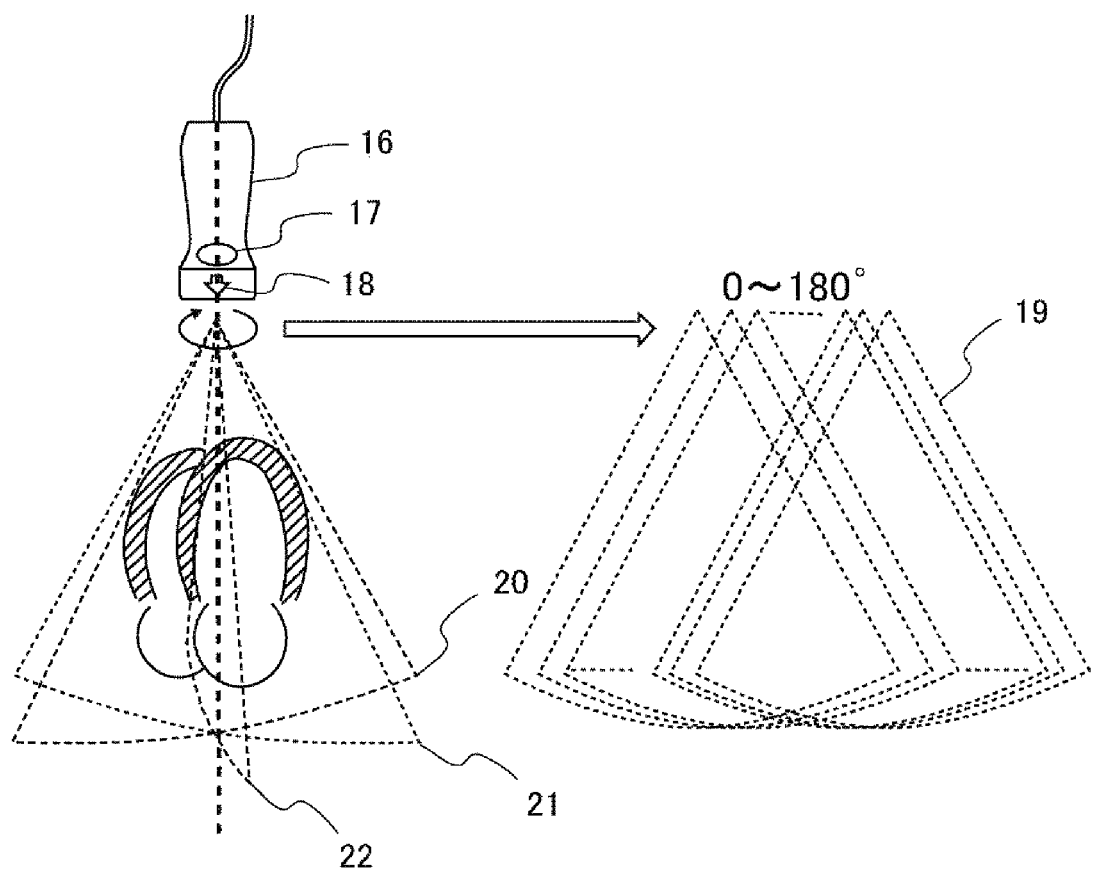
FIG. 2 is a diagram showing acquisition of a two-dimensional standard cross-section whose axis is set to an opening direction of a two-dimensional array probe.

It is the processing of extracting the images 20, 21, 22 having the rotational angles from the two-dimensional cross-section group 19 of FIG. 2.

The observation site indicating unit 4 is input equipment for indicating a site which an examiner intends to observe, and it comprises a touch panel, a switch, a keyboard, a trackball or the like. Furthermore, it also contains the processing of selecting a cross-section to be observed from a preset observation cross-section list 35 of FIG. 6.

The observation cross-section recognizing unit 5 recognizes the cross-section containing the site indicated by the observation site indicating unit 4 from the three-dimensional ultrasonic signal, and sets the image display parameters for the cross-section concerned. The image display parameters are used as image processing parameters such as a position and a gain to generate an observation target cross-sectional image from the data of the three-dimensional ultrasonic signal in the observation cross-sectional image generating unit 6. The image display parameters may be also used as image processing parameters such as threshold value setting and a point of view to generate a rendering image from the data of the three-dimensional ultrasonic signal in the rendering image generating unit 7.

The observation cross-sectional image generating unit 6 generates a two-dimensional cross-sectional image on the basis of the display parameters calculated in the observation cross-section recognizing unit 5 from the three-dimensional ultrasonic signal obtained by the three-dimensional ultrasonic signal generating unit 1. It generates an observation cross-sectional image 34 of FIG. 7.

The rendering image generating unit 7 generates a rendering image on the basis of the display parameters calculated in the observation cross-section recognizing unit 5 from the three-dimensional ultrasonic signal obtained in the three-dimensional ultrasonic signal generating unit 1. It generates a three-dimensional rendering image of a heart displayed in a sub window 31 for displaying the two-dimensional cross-sectional image of FIG. 7 or a rendering image of the observation cross-sectional image 34 of FIG. 7.

The image combination display unit 8 combines the images output from the two-dimensional standard cross-sectional image generating unit 3, the observation cross-sectional image generating unit 6 and the rendering image generating unit 7, and displays the composite image on the screen 30 of the ultrasonic diagnostic apparatus.

Figure 4:
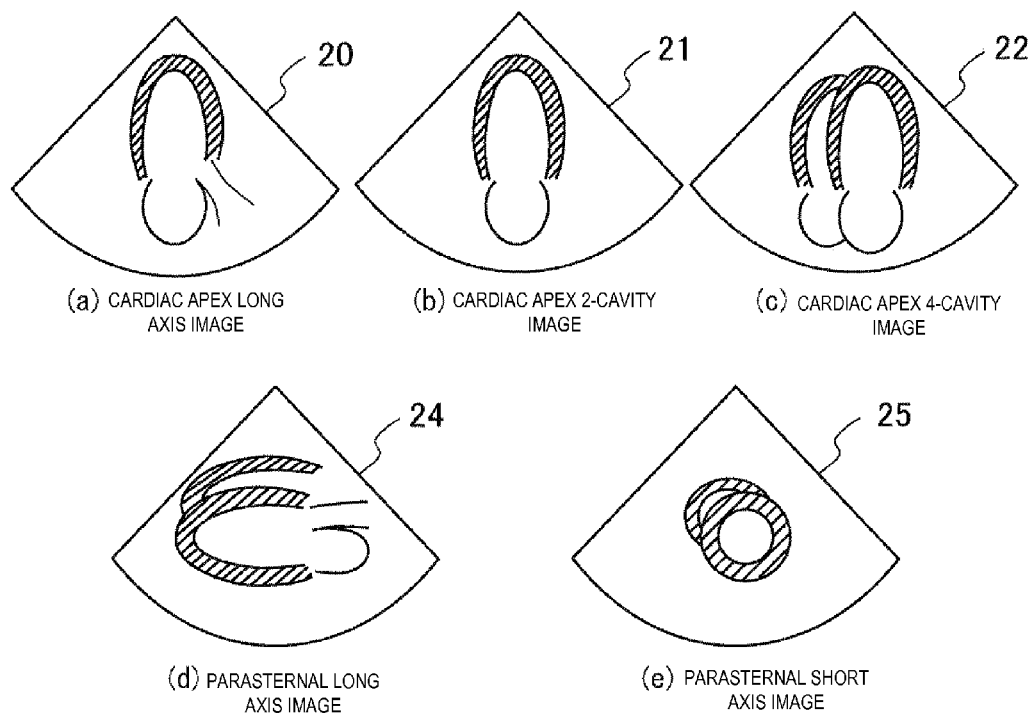
FIG. 4 is a diagram showing a two-dimensional standard cross-section.

The standard cross-section signal pattern storing unit 9 stores signal patterns of standard cross-sections (cardiac apex site 2-cavity image 21, cardiac apex site 4-cavity image 22, cardiac apex site long axis image 20, parasternal long axis image 24, parasternal short axis image 25 of FIG. 4) serving as references for matching to acquire the position of some cross-section of the standard cross-section signal from the three-dimensional signal in the two-dimensional standard cross-section recognizing unit 2.

Figure 3:
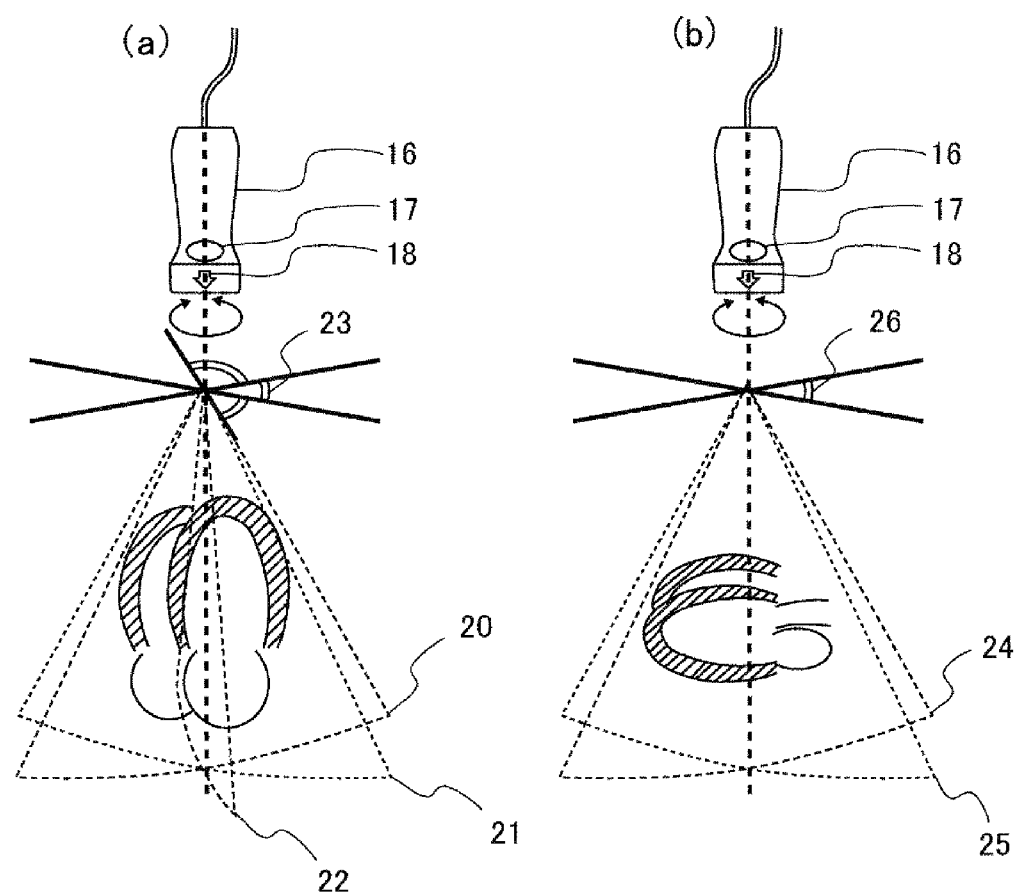
FIG. 3 is a diagram showing a rotational angle of the two-dimensional standard cross-section in a cardiac apex approach and parasternal approach.
Figure 9:
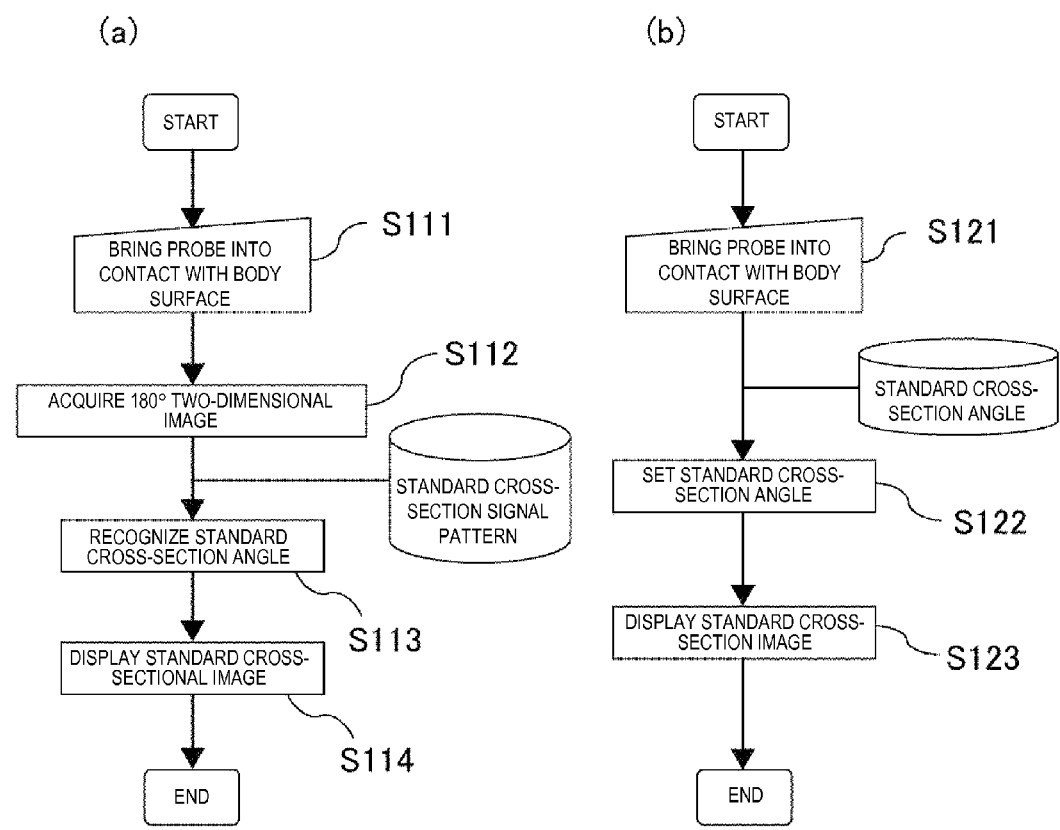
FIG. 9 is a diagram showing a processing flow for acquiring a two-dimensional standard cross-section from a three-dimensional signal.

The standard cross-section angle storing unit 10 stores standard positions (angles) of the standard cross-sections in the three-dimensional signal, and they correspond to the angles 23, 26 of FIG. 3. It is used when the angle is semi-automatically detected without executing the matching processing (FIG. 9(*b*)).

The standard cross-section angle calculating unit 11 executes the matching between the signal pattern stored in the standard cross-section signal pattern storing unit 9 and the two-dimensional signal pattern in the three-dimensional signal to determine the angle of the standard cross-section. That is, the matching operation is executed between the cross-section group 19 obtained through the rotation of 0 to 180° of FIG. 2 and the standard cross-section signal pattern of the standard cross-section signal pattern storing unit 9 to obtain the angle of the most matched cross-section.

Furthermore, a standard angle stored in the standard cross-section angle storing unit 10 and a contact angle to the body surface of the two-dimensional array probe are added to each other to determine a standard cross-section angle. That is, the direction of the heart is roughly known on the basis of the angle to the body surface of the probe. Accordingly, the angle of the standard cross-section is calculated by adding the standard cross-section angle.

The observation cross-section signal pattern storing unit 12 stores signal patterns of typical cross-sections which are optimally observed in heart ultrasonic examination (for example, a cross-section through which a mitral valve is easily observed, a cross-section through which papillary muscle is easily observed, etc.), and a pattern indicated by the observation site indicating unit 4 is called up. These patterns are stored in pairs with the position data stored in the observation cross-section position storing unit 13 and the display parameters stored in the display parameter storing unit 14.

The observation cross-section position storing unit 13 stores the positions in the three-dimensional signal of the typical cross-sections, and for example it indicates the distance from the probe to a cross-section, the position of a normal vector of the cross-section, etc.

The display parameter storing unit 14 stores parameters when an observation cross-section is displayed, and for example, they are a threshold value, a gain, a point of view, scale setting, etc. for rendering of a three-dimensional image.

Figure 10:
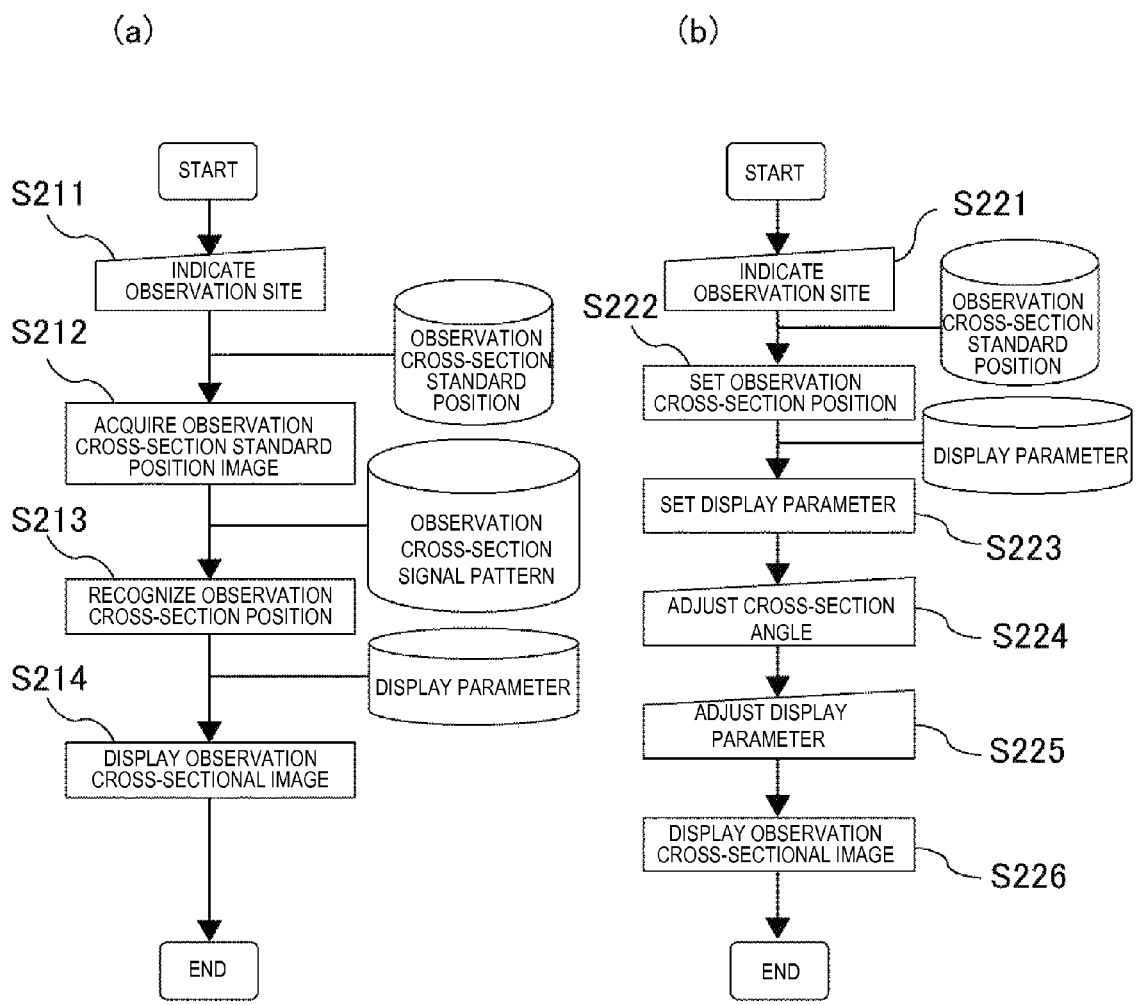
FIG. 10 is a diagram showing a processing flow for acquiring an observation cross-section from a three-dimensional signal.

The observation cross-section display parameter calculating unit 15 calls up the observation cross-section standard position of the observation cross-section position storing unit 13 for the site indicated by the observation site indicating unit 4 to roughly determine observation cross-section. Thereafter, an observation cross-section signal pattern is read out from the observation cross-section signal pattern storing unit 12, and the matching operation is executed between this signal pattern and the two-dimensional signal pattern in the neighborhood of the standard position to minutely determine the position of the observation cross-section signal. Alternatively, in the case of the semi-automatic processing (FIG. 10(*b*)), the observation cross-section position is determined as a standard cross-section position stored in the observation cross-section position storing unit 13. The parameter of the site indicated by the observation site indicating unit 4 is read out from the display parameter group stored in the display parameter storing unit 14. The parameter is used as an image processing parameter to generate an image in the observation cross-sectional image generating unit 6 and the rendering image generating unit 7.

The two-dimensional standard cross-sectional image generating unit 3, the observation cross-sectional image generating unit 6, the rendering image generating unit 7, the standard cross-section angle calculating unit 11 and the observation cross-section display parameter calculating unit 15 are normally constructed by CPU, and they are operated by programs.

(Overall Operation)

When the examiner brings the two-dimensional array probe into contact with the body surface, the two-dimensional standard cross-section recognizing unit 2 first calculates the rotational angle of the two-dimensional standard cross-section obtained by a cross-section rotating about the opening direction of the two-dimensional array probe. The two-dimensional standard cross-sectional image at the rotational angle position is obtained by the two-dimensional standard cross-sectional image generating unit 3. Subsequently, the observation cross-section recognizing unit 5 calculates the position in the three-dimensional signal of the site which the examiner intends to observe. The cross-sectional image at the position concerned is obtained by the observation cross-sectional image generating unit 6. Furthermore, a rendering image is generated in the rendering image generating unit 7 by using the standard display parameters of the observation site from the display parameter storing unit 14. Finally, screen display is performed by the image combination display unit 8 for combining the two-dimensional standard cross-sectional image, the observation cross-sectional image and the rendering image.

When the image combination display unit 8 combines the two-dimensional standard cross-sectional image, the observation cross-sectional image and the rendering image and screen-display them, it is unnecessary to subject all the images to composite display, and they may be suitably selected and displayed.

Furthermore, in the present invention, the image processing may be set as online processing in the ultrasonic diagnostic apparatus, however, it may be online processing or offline processing in the image processing apparatus.

Figure 6:
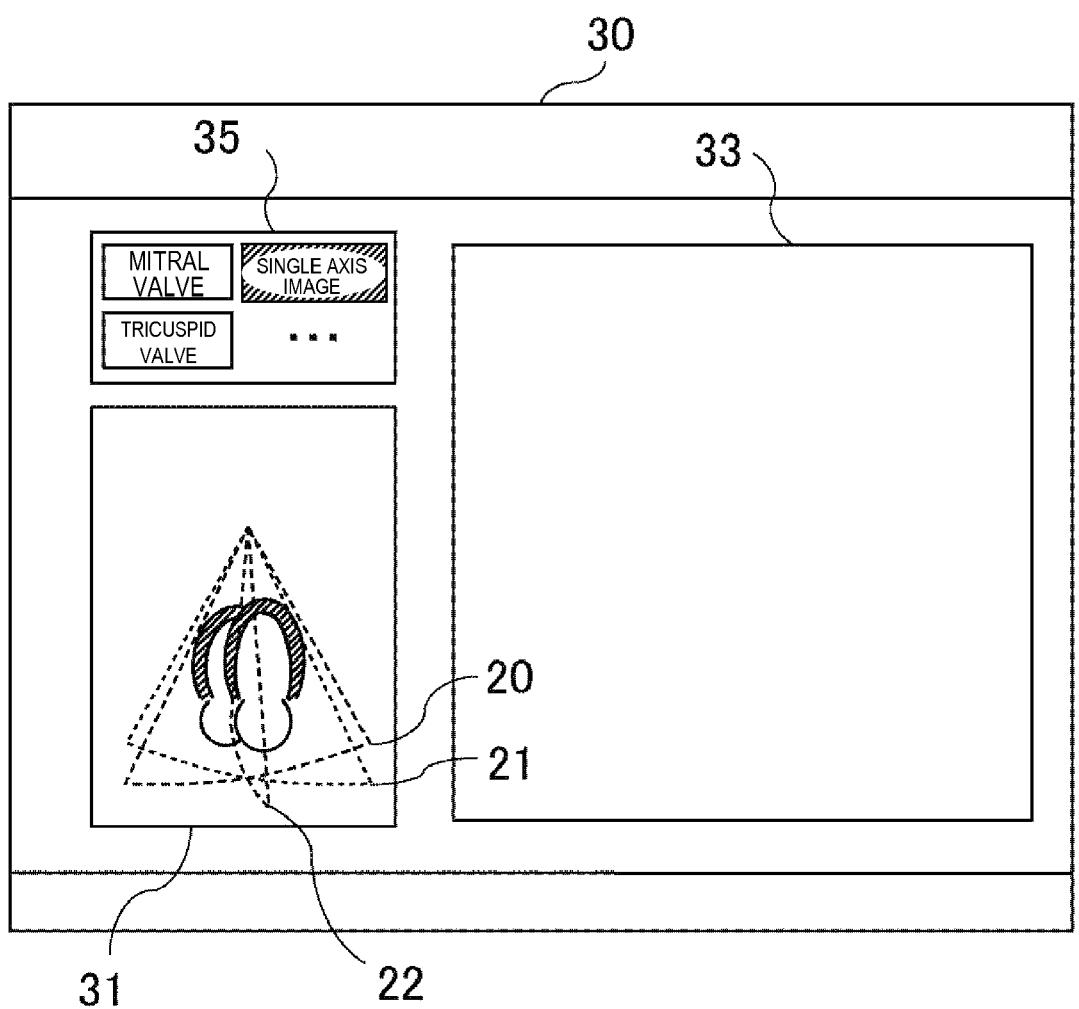
FIG. 6 is a diagram showing an observation cross-section selecting screen.

The operation on GUI will be described. When three-dimensional data are obtained, a screen of FIG. 6 is first displayed. As described above, the two-dimensional standard cross-sectional image is automatically recognized from the three-dimensional signal, superimposed on the three-dimensional image in the sub window 31 for displaying the two-dimensional cross-sectional image of FIG. 6 and displayed (20, 21, 22). Furthermore, a preset list 35 of cross-sections which are required to be observed.

Figure 7:
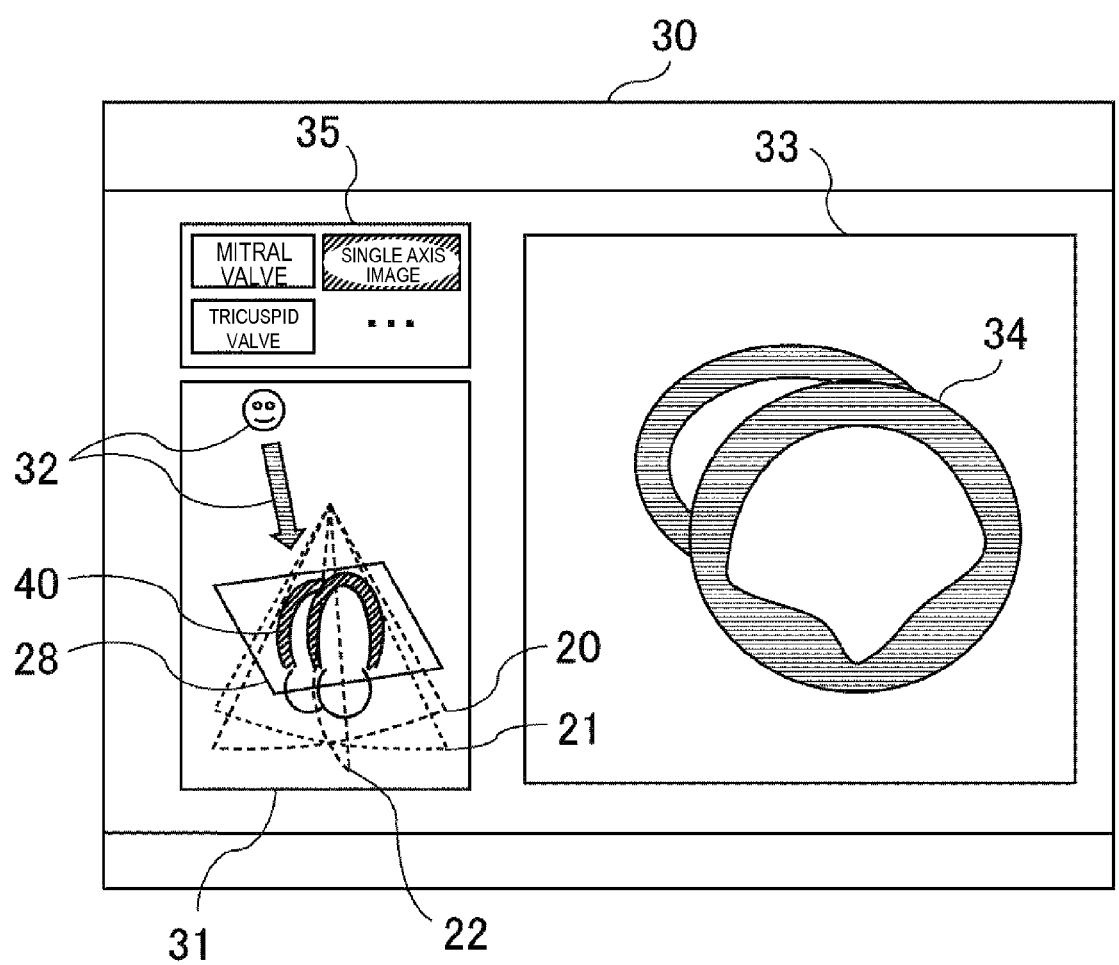
FIG. 7 is a diagram showing a display example of an observation cross-sectional image and a three-dimensional image.

Subsequently, a cross-section which is required to be observed is selected from the list 35. The examiner manually selects the cross-section by using input equipment or it is automatically selected at a specific time phase of an electrocardiogram signal. In FIG. 6, at the time when a short axis image is selected, the cross-section is displayed with being reversed or with blinking to make it easily comprehensible.

when an observation cross-section is selected as described above, an observed cross-section is recognized from the three-dimensional data, and the result is displayed as shown in FIG. 7. A cross-section which is required to be observed (in this example, short axis image) 34 is displayed in the observation cross-section displaying sub window 33 of FIG. 7. At the same time, the position 28 of the cross-section in the three-dimensional data is displayed in the two-dimensional cross-sectional image displaying sub window 31. The cross-section 28 is superimposed on the three-dimensional image, and the visual line direction 32 thereof is displayed.

The operation of the two-dimensional standard cross-section recognizing unit 2, the observation cross-section recognizing unit 5 and the image combination display unit 8 will be described in detail.

(Operation of Two-Dimensional Standard Cross-Section Recognizing Unit 2)

For the purpose of determining the direction of a two-dimensional standard cross-section of a heart in a three-dimensional signal, the two-dimensional standard cross-section recognizing unit 2 recognizes two-dimensional standard cross-sections (cardiac apex 2-cavity image 21, cardiac apex 4-cavity image 22, cardiac apex long axis view 20, parasternal long axis image 24, parasternal short axis view 25 of FIG. 4) in the plural cross-sections 19 rotated about the opening direction of the probe as an axis. This will be described with reference to FIGS. 2, 3 and 4 and the flowchart of FIG. 9.

Embodiment 1

This embodiment relates to a full-automatic operation by using signal pattern matching, and will be described along a flowchart of FIG. 9(a). First, the examiner brings the two-dimensional array probe into contact with the body surface (S111). The apparatus acquires a two-dimensional cross-section signal 19 over 0 to 180° obtained through the rotation about the opening direction of the two-dimensional array probe 16 as shown in FIG. 2 (S112). The matching operation between the standard cross-section signal pattern stored in the standard cross-section signal pattern storing unit 9 and the pattern of the cross-section signal is executed, and the angle of the most matched pattern is set as the angle 23 of the two-dimensional standard cross-section (S113). The matching operation is executed according to a known method such as correlation calculation or the like.

For example, as shown in FIG. 3(a), in the case of the cardiac apex approach, it is recognized which angle images the cardiac apex long axis image 20, the cardiac apex 2-cavity image 21 and the cardiac apex 4-cavity image 22 correspond to, whereby the angle relationship 23 of these images is obtained, imaging is performed by the two-dimensional standard cross-sectional image generating unit 3 with these images being set as standard cross-sections, and the images are displayed on the standard cross-sectional image displaying sub window 31 by the image combination display unit 8 (S114). As shown in FIG. 3(b), in the case of the parasternal approach, the angle relationship 26 between the parasternal long axis image 24 and the parasternal short axis image 25 is likewise acquired, and images are displayed.

Accordingly, the standard cross-section can be automatically displayed without making the examiner execute the setting operation. Furthermore, the standard cross-section position can be more accurately determined by using the signal pattern matching operation.

Embodiment 2

This embodiment relates to a semi-automatically operating method using a mark 18 provided to the housing of the two-dimensional array probe, and it will be described along a flowchart of FIG. 9(b). First, the examiner brings the two-dimensional array probe into contact with the body surface (S121). At this time, the probe is brought into contact with the body surface while the mark 18 attached to the probe faces a specific direction such as a direction to the body surface or the direction to a head portion. At this time, the positional relationship between the probe and the heart is physically determined, and thus a rough angle in the drawing direction of the heart is determined. The standard cross-section angle stored in the standard cross-section angle storing unit 10 is read out, and the angle of the standard cross-section is added in the drawing direction of the heart, thereby setting the standard cross-section angle (S122).

As in the case of the embodiment 1, they are set as the standard cross-sections, imaged by the two-dimensional standard cross-sectional image generating unit 3, and displayed on the standard cross-sectional image displaying sub window 31 by the image combination display unit 8 (S123).

Accordingly, the examiner can display the standard cross-section by a simple operation of bringing the two-dimensional array probe into contact with the body surface while setting the direction of the two-dimensional array probe to a specific direction. Not by using the image pattern matching, but by using the mark attached to the probe, the standard cross-section position can be easily determined.

(Operation of Observation Cross-Section Recognizing Unit 5)

Figure 5:
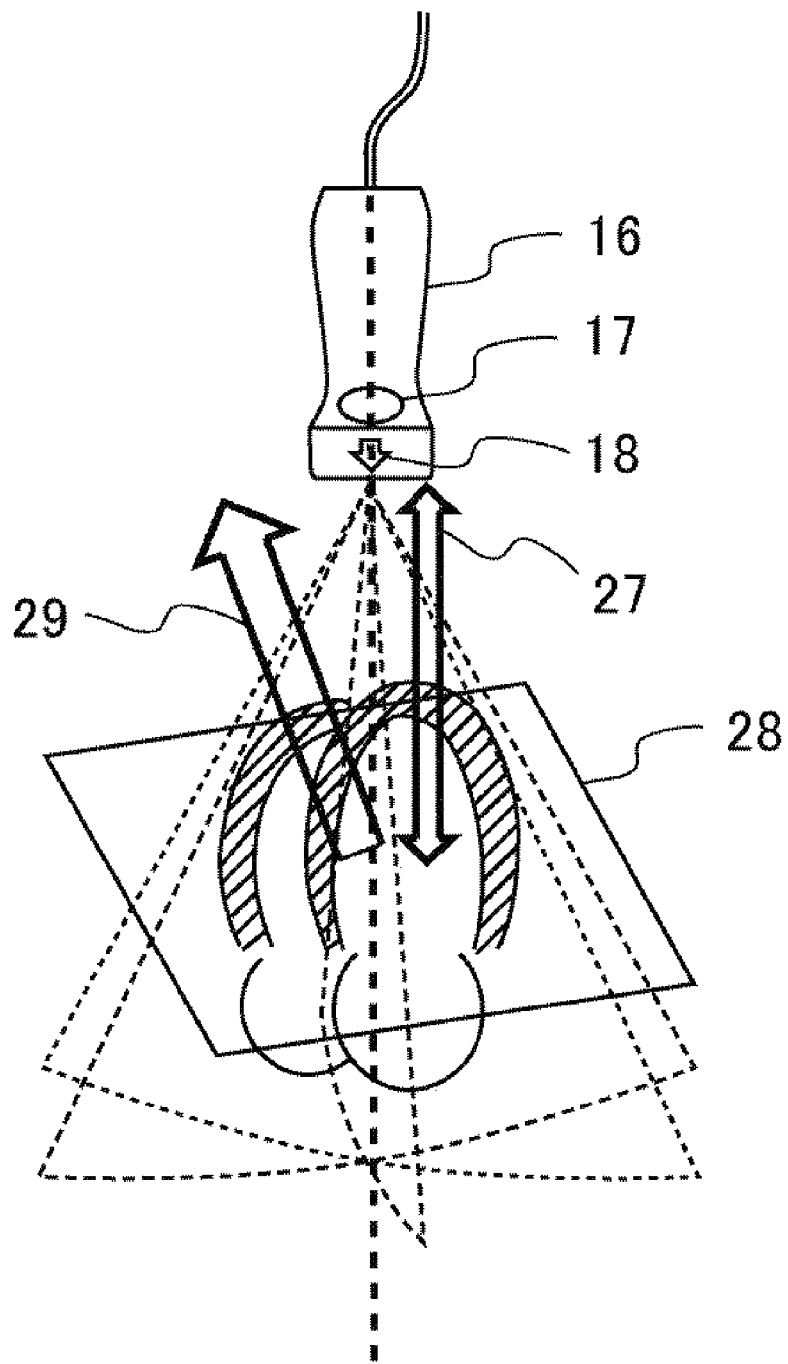
FIG. 5 is a diagram showing the positional relationship between a probe and an observation cross-section.

The observation cross-section recognizing unit 5 determines the position of the cross-section of a site which the examiner wishes to observe, in the three-dimensional signal. It will be described with reference to FIG. 5 and a flowchart of FIG. 10.

Embodiment 3

This embodiment relates to an automatically setting method using image pattern matching, and will be described along the flowchart of FIG. 10(a). First, the examiner indicates a desired observation site on the observation cross-section list 35 by using input equipment (S211). It is indicated by using a trackball or the like on the main body of the ultrasonic diagnostic apparatus or a site selecting switch 17 provided to the housing of the two-dimensional array probe shown in FIG. 5.

It may be indicated by at least one of a foot switch or voice recognition. When an electrocardiogram signal is input from the electrocardiograph, the previously preset observation cross-section may be switched in synchronization with a specific time phase of the electrocardiogram signal every time the specific time phase comes (every heartbeat or every several heartbeats).

Figure 12:
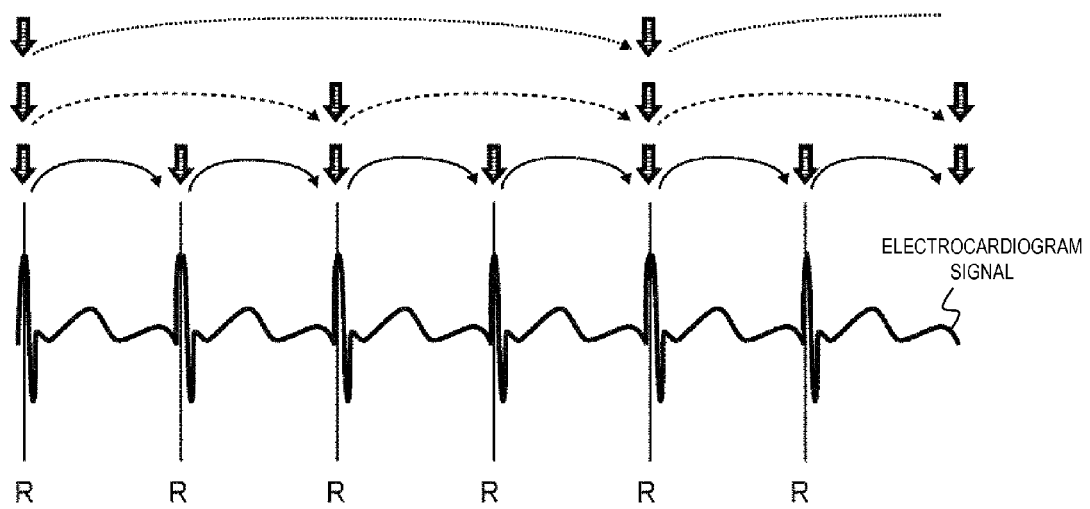
FIG. 12 is a diagram showing switching timing of an observation cross-section which is synchronized with an electrocardiogram signal.

For example, the time phase of R-wave of the electrocardiogram may be switched at every switching timing (indicated by a heavy-line arrow), or at 4 heartbeats (dashed-line arrow) as shown in FIG. 12. The preset cross-section is displayed in the style of a list on the screen like the observation cross-section list 35, and a currently selected cross-section is highlighted by reverse-display or the like at every time the cross-section is switched.

Figure 8:
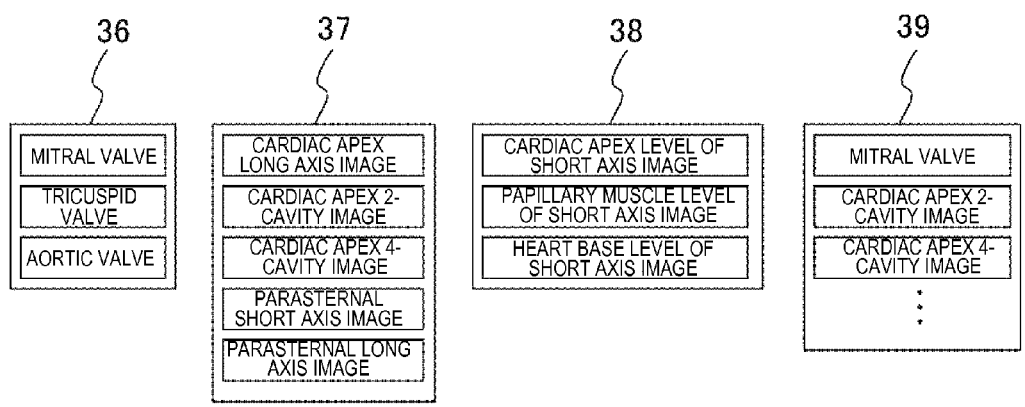
FIG. 8 is a diagram showing an observation cross-section preset example.

With respect to the preset, for example, a list 36 for only valves for observing valves, a list 37 for observing standard cross-sections, a list 38 for observing short axis images, etc. may be prepared as shown in FIG. 8. Furthermore, any list containing cross-sections necessary for specific patients, diseases, examinations may be created, and a list 39 of desired sites to be observed may be created along an examination order in advance. With respect to the indicated site, position information stored in the observation cross-section position storing unit 13 is read out, and a signal of the position is acquired (S212). The position information of an observation cross-section can be represented by the distance 27 from the probe, the normal vector 29 of the cross-section, however, it may be represented by a numerical value such as an angle from any reference position or the like. Since the direction (rotational angle) of the heart in the three-dimensional signal is calculated by the two-dimensional standard cross-section recognizing unit 2, for example, the normal vector is rotated by only this rotational angle, whereby the position of the observation cross-section is determined.

There is a case where only the above operation is insufficient for the precision of the position. Therefore, a fine adjustment is executed by signal pattern matching using an observation cross-section signal pattern stored in the observation cross-section signal pattern storing unit 12. A cross-section which is most coincident with the observation cross-section signal pattern is searched by moving the cross-section concerned at a minute distance or inclining the cross-section concerned at a minute angle in the three-dimensional ultrasonic signal in the neighborhood of the position of the cross-section acquired in S212, and the position concerned is recognized as the position of the observation cross-section (S213).

The matching operation is based on a known method such as correlation calculation. Display parameters for the site indicated by the observation site indicating unit 4 are taken out from the display parameter storing unit 14, images using the display parameters are generated in the observation cross-sectional image generating unit 6 and the rendering image generating unit 7, and the images are displayed in the image combination display unit 8 (S214).

According to this embodiment, the cross-section of the site indicated by the examiner can be automatically displayed.

Furthermore, by using the image pattern matching, the standard cross-section position can be more accurately determined. Furthermore, the display parameters are automatically set and thus an easily viewable image can be obtained simply. The operation can be easily performed in one hand by using the site selecting switch 17 provided to the housing of the probe.

Embodiment 4

This embodiment relates to a semi-automatically setting method based on the embodiment 3, and it will be described along a flowchart of FIG. 10(b). First, as in the case of the embodiment 3, by using input equipment, the examiner indicates a site which he/she wishes to observe (S221). The position information of the indicated site is read out from the observation cross-section position storing unit 13, and sets an observation cross-section at that position (S222). The display parameters for the indicated site are red out from the display parameter storing unit 14, set and image displayed on the screen (S223). Here, the position concerned is finely adjusted by using input equipment such as a trackball (S224). The position of the cross-section 28 of FIG. 7 varies in conjunction with the operation of the input equipment. The display parameters are finely adjusted simultaneously with the operation (S225), and an observation cross-sectional image 34 is displayed (S226).

According to this embodiment, after the examiner temporarily adjusts the observation cross-section to the position at which the examiner wishes to observe, the examiner can finely adjust the position manually. Accordingly, a labor of searching an observation target site from the overall three-dimensional signal which has been hitherto required can be eliminated, and an image can be displayed with a simple operation of performing only a local fine adjustment.

(Operation of Image Combination Display Unit 8)

The image combination display unit 8 combines the two-dimensional standard cross-sectional image, the observation cross-sectional image and the rendering image, and displays the images on the screen of the ultrasonic diagnostic apparatus. FIG. 7 shows a screen 30 of the display device of the ultrasonic diagnostic apparatus. A standard cross-sectional image output from the two-dimensional standard cross-sectional image generating unit 3 and a rendering image 40 of a heart are displayed on a sub window 31, and the visual line direction and the viewing point 32 are displayed in the normal vector on the window. The observation cross-sectional image 34 of the site indicated by the examiner is displayed on the sub window 33. Furthermore, the cross-section 28 represents the position at which the observation cross-section is located on the three-dimensional space. In FIG. 7, it is shown that the observation cross-sectional image 34 is the image at the position of the cross-section 28, and it is displayed so that the relationship between the three-dimensional signal and the observation site is easily understandable. In this example, the examiner has just indicated a papillary muscle level image of a short axis image of the left chamber of the heart, and a cross-section of a cardiac apex approach image is taken in the lateral direction to display a short axis image. A list 35 has a function of indicating a desired observation cross-section by input equipment, and preset cross-section types are displayed. The currently displayed cross-section is highlighted by reverse-display or the like.

Accordingly, according to this display method, the image to which the two-dimensional array probe is oriented and the image at the desired observation site are displayed at the same time, and the viewing point is displayed, whereby the positional relationship therebetween can be easily understood.

In the above embodiment, the foregoing description is made by applying a heart as an internal organ of the examinee, however, the embodiment may be applied to other internal organs, body parts. For example, the embodiment of this invention can be simply expanded to even an internal organ which is affected by heartbeat or body motion such as a liver.

The invention implemented by the inventors is specifically described on the basis of the embodiment. However, it is needless to say that the present invention is not limited to the embodiment and various modifications may be made without departing from the subject matter of the present invention.

DESCRIPTION OF REFERENCE NUMERALS 1 three-dimensional ultrasonic signal generating unit, 2 two-dimensional standard cross-section recognizing unit, 3 two-dimensional standard cross-sectional image generating unit, observation site indicating unit, 5 observation cross-section recognizing unit, 6 observation cross-sectional image generating unit, 7 rendering image generating unit, 8 image combination display unit, 9 standard cross-section signal pattern storing unit, 10 standard cross-section angle storing unit, 11 standard cross-section angle calculating unit, 12 observation cross-section signal pattern storing unit, 13 observation cross-section position storing unit, 14 display parameter storing unit, 15 observation cross-section display parameter calculating unit, 16 two-dimensional array probe, 17 observation site selecting switch, 18 two-dimensional array probe direction indicating mark, 19 two-dimensional cross-sectional image with opening direction of two-dimensional array probe set as axis, 20 cardiac apex long axis image, 21 cardiac axis 2-cavity image, 22 cardiac apex 4-cavity image, 23 rotational angle of two-dimensional standard cross-section in cardiac apex approach, 24 parasternal long axis image, 25 parasternal short axis image, 26 rotational angle of two-dimensional standard cross-section in parasternal approach, distance from probe to observation cross-section, 28 observation cross-section on two-dimensional image, 29 normal vector of observation cross-section, 30 display screen of ultrasonic diagnostic apparatus, 31 sub window for displaying two-dimensional cross-sectional image, 32 viewing point and visual line direction, 33 sub window for displaying observation cross-section, 34 observation cross-section image, 35 observation cross-section list, 36 valve observing preset, 37 standard cross-section observing preset, 38 short axis image observing preset, 39 preset for observing any cross-section, 40 three-dimensional rendering image of heart, 100 ultrasonic diagnostic apparatus, 200 examinee, 300 ultrasonic probe, 400 ultrasonic transmitting/receiving unit, 500 ultrasonic image constructing portion, 600 display unit, 700 controller, 800 control panel, 900 electrocardiograph

The invention claimed is:

1. An ultrasonic diagnostic apparatus, characterized by comprising:

means that acquires a three-dimensional ultrasonic signal of an internal organ of an examinee;

means that sets a direction of a two-dimensional standard cross-section of the internal organ;

means that adjusts display parameter of an image of a site which an examiner intends to observe;

means that generates a two-dimensional standard cross-sectional image from the three-dimensional ultrasonic signal on the basis of the set direction of the two-dimensional standard cross-section of the internal organ;

means that generates an observation cross-sectional image and a rendering image from the three-dimensional ultrasonic signal on the basis of the display parameters of the adjusted image; and display means that combines and displays the two-dimensional standard cross-sectional image, the observation cross-sectional image and the rendering image.

2. The ultrasonic diagnostic apparatus according to claim 1, wherein the means that sets the direction of the two-dimensional standard cross-section of the internal organ is pattern recognizing means for an ultrasonic three-dimensional signal.

3. The ultrasonic diagnostic apparatus according to claim 2, wherein the pattern recognizing means for the three-dimensional signal is means that recognizes a plurality of two-dimensional cross-section signals obtained by electrically rotating a two-dimensional array probe about a direction vertical to a body surface.

4. The ultrasonic diagnostic apparatus according to claim 2, wherein the three-dimensional signal pattern recognizing means determines a rotational angle of a standard cross-section used for an examination based on a two-dimensional image of an internal organ.

5. The ultrasonic diagnostic apparatus according to claim 1, wherein the means that sets the direction of the two-dimensional standard cross-section of the internal organ contains a mark that is attached to a housing of a two-dimensional array probe and represents a direction of the two-dimensional array probe to the body surface.

6. The ultrasonic diagnostic apparatus according to claim 5, wherein the means that sets the direction of the two-dimensional standard cross-section of the internal organ determines the direction as a standard rotational angle with the direction of the mark set as a reference.

7. The ultrasonic diagnostic apparatus according to claim 1, wherein the image display parameter adjusting means has a user interface through which an examiner indicates a type of a site which the examiner wishes to observe, has means that recognizes an observation position on the basis of matching operation with a standard signal pattern to the indicated type of the site or means that selects standard position data stored in a storage device, and has means that selects an image display parameter associated with the type of the site stored in the storage device.

8. The ultrasonic diagnostic apparatus according to claim 7, the user interface for indicating the type of the site which the examiner wishes to observe has means that switches on the basis of at least one of selection from a menu on an apparatus screen, a switch mechanism mounted on a probe housing, a foot switch, voice recognition and synchronization of an electrocardiogram signal.

9. The ultrasonic diagnostic apparatus according to claim 8, wherein the means that switches the type of the cross-section on the basis of the synchronization of the electrocardiogram signal has a sequence function of successively switching preset cross-sectional types in synchronization with a specific time phase of an electrocardiogram.

10. The ultrasonic diagnostic apparatus according to claim 7, wherein the observation position recognizing means based on the matching operation with the standard signal pattern to the type of the indicated site sets a signal pattern stored in the storage device to a position recognized through signal pattern recognition calculation from the obtained three-dimensional signal.

11. The ultrasonic diagnostic apparatus according to claim 7, wherein the means that selects standard position data stored in the storage device selects position data corresponding to the indicated site type from a standard position data group associated with each site stored in the storage device.

12. The ultrasonic diagnostic apparatus according to claim 7, wherein the means that selects the image display parameters associated with the site type stored in the storage device selects each parameter of an indicated site from a standard gain, a viewing point, rendering and scale parameter group associated with the site type stored in the storage device.

13. The ultrasonic diagnostic apparatus according to claim 1, wherein the display means simultaneously displays, on a display device, a two-dimensional standard cross-sectional image obtained along the direction of a two-dimensional array probe and an image which an examiner wishes to observe, and displays a cross-section being observed, a viewing point and a visual line direction on the two-dimensional standard cross-sectional image.

14. An image processing apparatus used to process a three-dimensional ultrasonic signal of an internal organ of an examinee, characterized by comprising:

means that sets a direction of a two-dimensional standard cross-section of the internal organ;
means that adjusts display parameter of an image of a site which an examiner intends to observe;
means that generates a two-dimensional standard cross-sectional image from the three-dimensional ultrasonic signal of the internal organ on the basis of the set direction of the two-dimensional standard cross-section of the internal organ;
means that generates an observation cross-sectional image and a rendering image from the three-dimensional ultrasonic signal of the internal organ on the basis of the display parameters of the adjusted image; and
display means that combines and displays the two-dimensional standard cross-sectional image, the observation cross-sectional image and the rendering image.

15. The image processing apparatus according to claim 14, wherein the means that sets the direction of the two-dimensional standard cross-section of the internal organ is pattern recognizing means for an ultrasonic three-dimensional signal.

* * * * *